US00PP08574P

United States Patent [19]

Drewlow

[11] Patent Number: Plant 8,574

[45] Date of Patent: Feb. 1, 1994

[54] POINSETTIA PLANT NAMED BLITZEN

[75] Inventor: Lyndon W. Drewlow, Ashtabula, Ohio

[73] Assignee: Mikkelsens, Inc., Ashtabula, Ohio

[21] Appl. No.: 22,344

[22] Filed: Feb. 24, 1993

[51] Int. Cl.[5] ..... A01H 5/00
[52] U.S. Cl. ..... Plt./86.2
[58] Field of Search ..... Plt. 86.2

*Primary Examiner*—James R. Feyrer
*Attorney, Agent, or Firm*—Foley & Lardner

[57] ABSTRACT

A new and distinct cultivar of poinsettia plant named Blitzen, produced by grafting a seedling from the cross described to a plant of White Rochford for the purpose of transferring the excellent branching characteristics of White Rochford. Blitzen is characterized by its relatively large white bracts, strong, vigorous growth habit, early flowering, excellent branching, excellent foliage retention, resistance to heat delay of flower bud initiation when night temperatures are above 23° C., dark green leaves, and small cyathia cluster.

2 Drawing Sheets

The present invention relates to a new and distinctive cultivar of poinsettia plant, botanically known as *Euphorbia pulcherrima,* and referred to by the cultivar name Blitzen.

Blitzen was developed by me through controlled breeeding by crossing Mikkelsen Seedling No. 87-143-1 (seed parent) with Mikkelsen Seedling No. 87-278-1 (pollen parent). One of the seedlings from the cross was characterized by white bracts and poor branching and was identified as seedling No. 88-153-1. This seedling was then grafted to the excellent branching type cultivar White Rochford (not patented) in an attempt to transfer the branching habit of White Rochford to 88-153-1. The graft was successful, resulting in the new seedling having the branching habit of White Rochford and retaining all other desirable characteristics of the new white seedling.

Asexual reproduction by stem cuttings in a greenhouse in Ashtabula, Ohio, and has shown that the unique features of this new poinsettia are stabilized and are reproduced true to type in successive propagations.

The following characteristics distinguish Blitzen from both its parent cultivars and other cultivated poinsettia of this type known and used in the floriculture industry.

1. When 5 or more nodes are left after a pinch (apical tip removal), Blizen will develop full length shoots from each node like White Rochford and White Yuletide (U.S. Plant Pat. No. 8,018), while the original seedling 88-153-1 will develop a full length shoot from only the upper 3 or 4 nodes, with the balance of shoots being greatly repressed.

2. Plants of Blitzen are 20 to 22 cm in height, and are shorter than the 88-153-1 seedling at 25 to 27 cm when similar size plants are left after pinching. The reason for this is that there is little or no apical dominance in the branched types. Thus, lower branches may grow longer than top branches instead of 3 or 4 shoots becoming dominant. White Yuletide at 24 to 26 cm and White Rochford at 36 to 38 cm are taller but branched plants.

3. Blitzen has dark green (147A, RHS) leaves which are slightly lighter in color than the leaves of the original seedling 88-153-1, but darker than the leaves of White Yuletide and White Rochford. However, all would be generally classified as 147A.

4. Blitzen is more tolerant than 88-153-1 to low light levels and high temperature conditions of the average home, as leaves do not drop like 88-153-1 under these conditions. When kept moist, Blitzen has excellent foliage retention, similar to White Rochford and White Yuletide.

5. Blitzen and seedling 88-153-1 have bract coloration 155B white, with White Yuletide being 155A to 157B, and White Rochford 155A.

6. Blitzen has a cyathia cluster (flowers in center of bract) that is slightly smaller in number and diameter (3–4 cm) than the original seedling 88-153-1; larger than White Yuletide, but not as large as White Rochford.

7. Blitzen is resistant to heat delay of flower bud initiation under night temperatures above 23° C., similar to seedling 88-153-1 and White Yuetide. On the other hand, White Rochford is very susceptible to heat delay. Heat delay resistance is of great commercial importance, especially in the southern United States and where the autumn seasons in the north are warmer than normal.

8. Bract size of Blitzen at 24 to 26 cm is larger than the bracts of White Rochford at 20 to 23 cm, and similar to White Yuetide. Bracts of Blitzen are somewhat concave while the bracts of White Rochford and White Yuetide are generally flat with slight reflexing. The cyathia of Blitzen does not split apart like White Rochford but remains in a tight cluster at center of bract like White Yuletide.

9. All other characteristics of Blitzen are similar to the orignal seedling, 88-153-1, such as early flowering under natural short days, similar shaped leaves and bracts, and retention of cyathia under stress conditions.

The accompanying colored photographs illustrate the overall appearance of Blitzen, with the colors being as true as it is reasonably possible to obtain in color reproductions of this type.

The photograph on sheet 1 is a front perspective view showing the foliage and bracts of a typical plant of Blitzen.

The photograph on sheet 2 is a top perspective view of the plant, showing the bracts more clearly. The photographs were taken on Nov. 26, 1991 in a rigid fiberglass greenhouse on an overcast day in Ashtabula, Ohio.

The following detailed description of my new cultivar is based on plants produced in greenhouses in Ashtabula, Ohio during the Fall season of the year. Plants were grown in 15 cm pots and measurements were taken seventeen (17) weeks after rooted cuttings were planted. Height measurements were taken from the soil line of the container. The plants were grown at 64°-68° F. night temperatures, with 3500-4000 foot candles of light, and with 250 ppm Nitrogen, 75 ppm Potassium, and 250 ppm Phosphorous nutritional levels, with trace elements added. Habit of growth, foliage coloration, leaf variegation, size of leaves and flower size will be influenced by nutritional and environmental conditions, without, however, any variation in genotype.

Color references are made to the Royal Horticultural Society Colour Chart (RHS) except where general terms of ordinary dictionary significance are used.

Parentage: Controlled cross between female Mikkelsen Seedling No. 87-143-1 and male Mikkelsen Seedling No. 87-278-1;, with resulting seedling being grafted to White Rochford to produce a branching type plant.

Propagation:

A. *Type cuting.*—Stem 5 to 6 cm long.

B. *Time to root.*—14 days at 21° C. Summer; 18 days at 21° C. Winter.

C. *Rooting habit.*—Abundant, thick, fibrous roots.

Plant description:

A. *Form.*—Upright; when apical meristem is removed (pinching) leaving 5 or more nodes above soil line of pot, generally all lateral shoots will emerge and develop.

B. *Habit of growth.*—Strong stems hold bracts up for good flower display. Good branch main stem angle reduces breakage in shipping. Bottom stems break first and elongate faster than upper stems, resulting in the upright growth habit, with bract display on upper ⅔ of plant. Growth is vigorous and Blitzen can easily be grown with use of proper scheduling system without chemical growth regulators.

C. *Foliage.*—Leaves are alternate and borne on 4.0 to 4.5 cm long petioles which have a yellow green cast. The last 3 to 4 leaves before true bract leaves also turn the same color white as the bracts. 1. Size: Mature leaves are on average 11 to 12 cm long and 6 to 7 cm wide at broadest point near basal area of leaf. 2. Shape: Ovate to lanceolate with acuminate apex and rounded base. 3. Texture: Upper glabrous; lower glabrous and rugose because of protuding veins. 4. Margin: Entire. 5. Color: Young foliage, top side, 144A. Under side, 146C. Mature foliage, top side, 147A. Under side, 147B.

Flowering description:

A. *Flowering habits.*—Earlier flowering than most older commercial cultivars, apparently having a longer critical daylength for flower initiation. Under controlled daylength, development time is approximately 8½ weeks, but appears even earlier because last 3 to 4 true leaves turn white before rest of bracts fully expands. Early flower initiation is of commercial significance. Bracts in involucre face somewhat upward.

*Natural flowering season.*—November 15 to 22 under Ohio conditions. Flowering time under 11 hours of daylength at 20° C. is 8½ weeks.

C. *Cyathia.*—Are stress tolerant, remaining in the center of involucre for a considerable time under low fertility, low light and high temperature conditions. Severe drying may cause them to drop.

D. *Cyathia borne.*—Stay closely clustered without growing apart (splitting). Usually 3 to 4 cm in diameter. Flowering can be initiated any time of the year by controlling the daylength to approximately 11 hours total; will continue to initiate until daylength is greater than approximately 13 hours.

E. *Quantity of cyathia.*—Highly dependent on cultural practices and can vary from minimum of 5 to 8 to more than 15.

F. *Bracts.*—1. Shape: Ovate to oblong, first bracts 9 to 10 cm long and 4.5 to 5.0 wide on 1.0 to 1.5 cm petioles; later bracts 6.0 to 7.0 long, 3.0 to 3.5 wide on 0.5 to 1.0 cm petioles. 2. Color at maturity: Upper side 155B, under side 155A, with midrib and major veins being greenish in color; young bracts are 155A, upper side. 3. Number of bracts; 15 to 20 normal number but could be more or less depending on growing conditions, for example, if plants are pinched and growth regulators are used.

G. *Reproductive organs.*—1. Stamens: Numerous. a. Anther shape: Oblong, color whitish. b. Filament color: Whitish. c. Pollen color: Yellow. 2. Pistels: a. Stigma shape: Forked, color yellow green. b. Style color: Yellow green. c. Ovaries: 3, celled, 3 mm when stigma is receptive, green in color. 3. Nectar cups: Usually 1, nectar readily available on mature cyathia.

Disease resistance: Bracts are resistant to botrytis damage, even on older bracts after pollen shed; small cyathia area helps prevent botrytis after nectar cups start exuding honey-like substance.

OTHER IMPORTANT CHARACTERISTICS

1. Upright compact habit with strong branches holds up bracts well and makes sleeving for shipping faster and easier with a minimum of breakage.
2. Dark green foliage give plant a healthy look.
3. Earlier flowering under natural short day conditons eliminates the need for black cloth for mid-November sales.
4. Compact growth habit allows crop to be grown without growth regulators, thereby eliminating both a crop expense and a potential environmental hazard.

I claim:

1. A new and distinct cultivar of poinsettia plant named Blitzen, as illustrated and described.

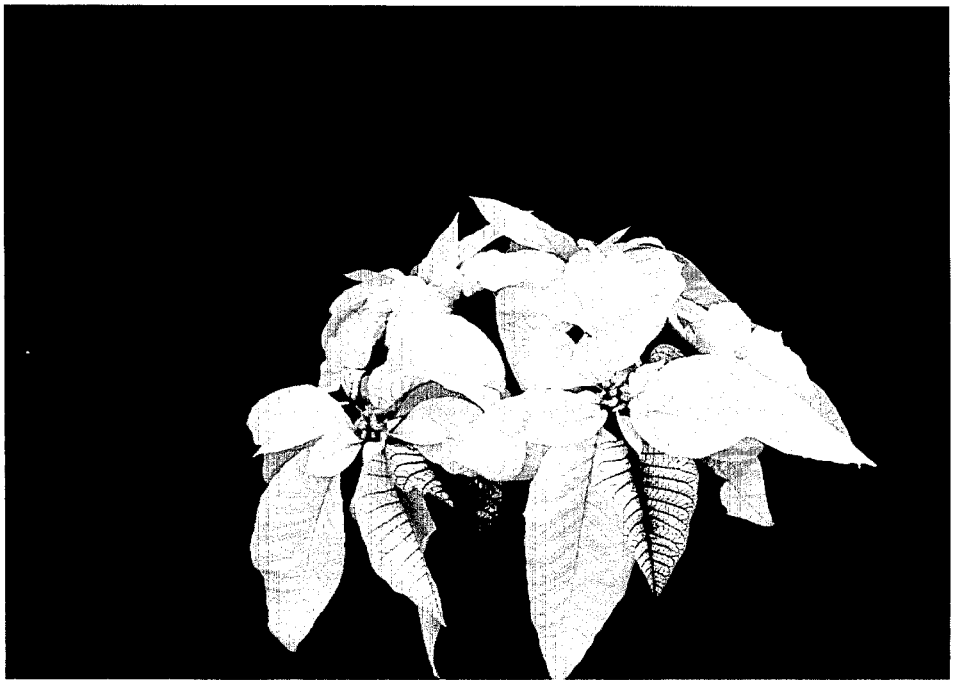

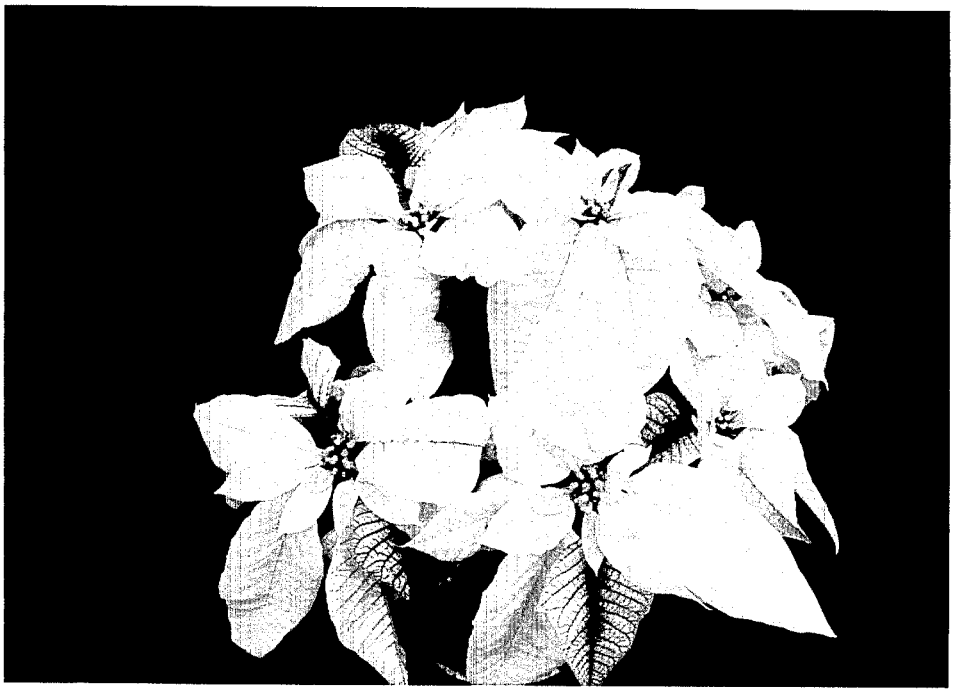

* * * * *